US 6,746,686 B2

(12) United States Patent
Hughes et al.

(10) Patent No.: US 6,746,686 B2
(45) Date of Patent: Jun. 8, 2004

(54) COATED IMPLANTS

(75) Inventors: Laurence Gerald Hughes, Surrey (GB); Terrence Albert Vick, Surrey (GB); Jin Hai Wang, Surrey (GB)

(73) Assignee: Biocompatibles UK Limited, Surrey (GB)

(*) Notice: Subject to any disclaimer, the term of this patent is extended or adjusted under 35 U.S.C. 154(b) by 0 days.

(21) Appl. No.: 09/937,224
(22) PCT Filed: Jan. 24, 2001
(86) PCT No.: PCT/GB01/00281
§ 371 (c)(1), (2), (4) Date: Sep. 24, 2001
(87) PCT Pub. No.: WO01/52915
PCT Pub. Date: Jul. 26, 2001

(65) Prior Publication Data
US 2003/0086957 A1 May 8, 2003

(30) Foreign Application Priority Data
Jan. 24, 2001 (EP) .............................. 00300509

(51) Int. Cl.$^7$ ................................. A61F 2/02
(52) U.S. Cl. .................. 424/425; 424/423; 424/424
(58) Field of Search ................. 424/423, 424, 424/425

(56) References Cited
U.S. PATENT DOCUMENTS

| 5,342,621 A | 8/1994 | Eury |
| 5,674,192 A | 10/1997 | Sahatjian et al. ............. 604/28 |
| 5,783,650 A | 7/1998 | Bowers et al. |
| 5,954,706 A | 9/1999 | Sahatjian ..................... 604/509 |
| 5,965,720 A | 10/1999 | Gryaznov et al. .......... 536/23.1 |
| 6,251,964 B1 | 6/2001 | Porssa et al. |

FOREIGN PATENT DOCUMENTS

| DE | 197 13 214 | 12/1998 |
| EP | 0 809 999 | 12/1997 |
| EP | 0 861 858 | 9/1998 |
| EP | 0 873 732 A1 | 10/1998 |
| WO | 94/15646 | 7/1994 |
| WO | 97/47253 | 12/1997 |
| WO | 98/15575 | 4/1998 |
| WO | 98/22162 | * 5/1998 |
| WO | 98/22516 | 5/1998 |
| WO | WO 98/22517 | 5/1998 |
| WO | 98/36784 | 8/1998 |
| WO | 01/01957 | 1/2001 |

OTHER PUBLICATIONS

International Preliminary Examination Report dated Apr. 18, 2002.

* cited by examiner

Primary Examiner—Carlos Azpuru
(74) Attorney, Agent, or Firm—Sughrue Mion, PLLC

(57) ABSTRACT

An implant, usually a stent, has a coating of a cross-linked water swellable polymer matrix preferably having a dry thickness of at least 0.1 μm, and a pharmaceutically active compound, the polymer having pendant cationic and pendant zwitterionic groups. The active is usually an anionic compound such as a nucleic acid. The polymer is peferably formed from 2-methacyloyloxyethyl-2'-trimethylammoniumethyl phosphate inner salt, trialkylammoniumalkyl(meth)acrylate and a cross-linkable monomer such as ω(trialkoxysilyl)alkyl(meth)acrylate, optionally with a termonomer such as a higher alkyl(meth) acrylate. The stent is coated with polymer, cross-linked then contacted with a solution or dispersion of active compound in a solvent which swells the polymer wehereby the active is absorbed into the polymer matrix. The stent is delivered by usual means into a body lumen and the active is released over an extended period of time into the wall of the lumen and/or fluid flowing therein.

50 Claims, 12 Drawing Sheets

Figure 1:
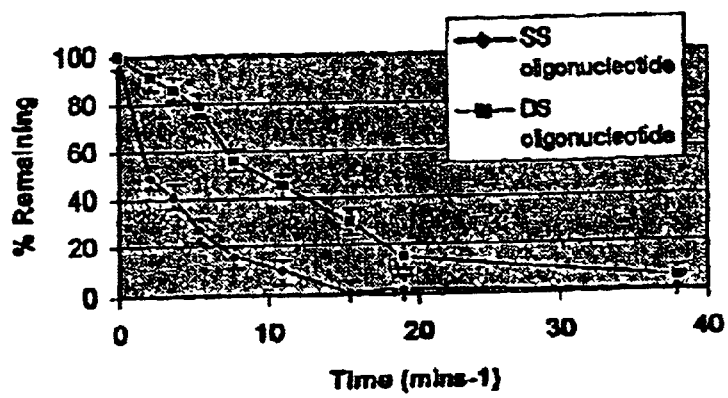

Effect of oligomer concentration (initial activity) on stent loading

Effect of temperature of 15-mer loading

Loading of 15 mer (initial activity: 211 µCi) on PC coated Biodyviso stents

Stent treatment (% of CM in polymer and pretreatment) [polymer]

Yields of loading for the 32P-15 mers onto the PC Biodivysio stents

Concentraion (weight [2.6%] [polymer]

Yields of loading for the 32P-32mers onto the PC Biodivysio stents

CM concentration (%)

Elution profile of 15 mer loaded PC stents

Time (minute)

Elution of 32P labelled oligonucleotides (15 and 32 mers) loaded on PC Biodyvisio stents after incubation in blood at 37°C.

Remaining activities (µCi) 30 minutes after 15 mer loaded PC stent (15 x 3.5 mm) deployment in the pisg's LCX arter (initial stent activity: 12 µCi)

Elution of 23p labeled 32 mers from polymer 2.2 coated Biodyvisio PC stent deployed in pig's LAD artery In vivo follow-up of coated stents In vivo follow-up of coronary arteries Radioactive heparin release profile (2.2)

COATED IMPLANTS

The present invention relates to implants, especially stents, primarily for introduction into blood vessels, but which are also useful for introduction into other body lumens, which have a coating of a biocompatible hydrogel polymer, used as a reservoir from which drugs are delivered direct to the wall of the vessel in which the stent is positioned.

In our earlier WO-A-0101957 which was not published at the priority date hereof, we describe stents with coatings of biocompatible crosslinked polymers, which are swollen in drug containing solutions immediately before delivery into a patient. Drug is absorbed into the swollen hydrogel, and is released over extended periods of time from the implanted stent. The system described in those applications has been approved for marketing in Europe for use with drugs having molecular weights up to 1200D. Examples of such drugs include dipyridamole, dicloxacillin, vitamin B12 and angiopeptin.

In our earlier application number WO-A-9822516, we describe polymers formed from ethylenically unsaturated monomers including a cationic monomer and a zwitterionic monomer, useful for providing biocompatible coatings on various substrates. The cationic polymer attracts anionic mucopolysaccharide. A stent coated with the polymer may be used as a scavenging device to remove systemic heparin from the circulation of a patient. Alternatively, it is suggested that the device may be preloaded with, for instance, heparin to allow extended release of the drug into a circulation from an implanted stent.

In EP-A0809999, heparin is covalently bound to a stent using the Carmeda CH5 heparin coating system.

Angiogenic compounds have been delivered from stents to treat stenotic lesions. In WO-A-97/47253, for instance, angiogenic compounds are delivered following radiation treatment of the heart. Delivery may be from a stent coated with a polymer.

In U.S. Pat. No. 5,954,706 an anionic hydrogel is coated on to a stent, a monovalently cationic compound, such as a benzalkonium compound, is coated over the hydrogel and heparin is contacted and electrostatically bound to the cationic compound.

Sense and anti-sense DNA have been delivered from stents, for instance in WO-A-98/15575. The DNA may encode an angiogenic protein.

In U.S. Pat. No. 5,674,192 nucleic acids and monoclonal antibodies delivered by squeezing them from a swollen hydrogel coating on a balloon catheter. The nucleic acids may be antisense oligonucleotides or viral vectors. The hydrogel may be a polycarboxylic acid such as polyacrylic acid. Nucleic acid is delivered to cells of the vessel wall.

A new implant according to the invention has a coating on its external surface comprising:
  a) a crosslinked, water swellable polymer matrix having a dry thickness of at least 0.1 $\mu$m, and
  b) a pharmaceutically active compound
  in which the polymer has pendant zwitterionic groups and pendant cationic groups.
The implant is preferably a stent.

The invention is of particular utility for delivering pharmaceutically active compounds which are anionic under physiological conditions. The invention is also of particular value for higher molecular weight active compounds, especially having molecular weights of more than 1000D, more preferably more than 1200D, for instance 5000D or more.

The pharmaceutical active may be a protein, for instance an antibody or fragment thereof. Such compounds are usually and preferably in this invention anionically charged in physiological environments. The invention is of particular value for active compounds comprised of nucleic acids. The nucleic acids may be DNA or RNA, and may be linear or circular, single or double stranded. The nucleic acid may encode a pharmaceutically useful polypeptide or protein, or it may be an anti-sense oligo-nucleotide, used to control the gene of interest in the cell to which the nucleic acid is delivered. A nucleic acid encoding a useful polypeptide or protein may include control regions, or other sequences to allow expression of the gene and/or its delivery into the cell and/or transport of the protein to its target. Oligo nucleotides conjugated to other actives eg for targeting purposes, are also usefully delivered by this invention.

One particularly interesting class of gene delivered by the invention encodes angiogenic factors, such as vascular endothelial growth factors or fibroblast growth factors, or platelet derived growth factors. Suitable control sequences may direct expression in smooth muscle cells, specifically. For instance the control sequences may be as described in WO-A-98/15575. Oligonucleotides which may be used in the present invention have, for instance, at least 5 bases, preferably at least 15 bases.

According to a second aspect of the invention, a new implant has a coating on its external surface comprising:
  a) a crosslinked, biostable polymer matrix and
  b) a pharmaceutically useful nucleic acid,
in which the polymer has pendant zwitterionic groups and pendant cationic groups.

According to a third aspect of the invention, a new implant having a coating on its external surface comprising:
  a) a cross-linked, biostable polymer and
  b) a pharmaceutically active compound which is a protein which is anionically charged at physiological pH in which the polymer has pendant zwitterionic groups and pendant cationic groups.

In the second and third aspects it is preferred, thought not essential for the polymer matrix to have a dry thickness of at least 0.1 $\mu$m. Furthermore it is preferred but not essential for the polymer matrix to be water swellable. We have found that anionic actives such as nucleic acid and proteins, especially those having molecular weights above 1 KD, primarily become adsorbed at the surface of a polymer having cationic groups and zwitterionic groups, with little being adsorbed into the body of the polymer. For this reason the swellability and the thickness are of lesser importance than in the first aspect.

The implant is preferably a stent. In the rest of this specification the device is described in terms of stents, but it will be understood other implants may be substituted for stents.

The crosslinking of the polymer matrix stabilises the coating on the stent, rendering it biostable. Adjustment of the crosslink density provides some control over the extent to which the polymer swells in a swelling solvent, generally aqueous in nature. The crosslink density furthermore effects the pore size of the polymer matrix. It is believed that the pore size, in turn, effects the maximum molecular size of pharmaceutically active compounds which may be absorbed into the matrix which is of particular relevance to the first aspect of the invention. It is preferred that the polymer be formed from ethylenically unsaturated monomers including less than 20% by mole of crosslinkable monomer.

The polymer used in the present invention is preferably formed from ethylenically unsaturated monomers including a) a zwitterionic monomer of the formula I $$YBX \qquad\qquad I$$

wherein B is a bond or a straight or branched alkylene, alkylene-oxa-alkylene or alkylene-oligooxa-alkylene group, any of which optionally include one or more fluorine substituents;

X is an organic group having a zwitterionic moiety; and

Y is an ethylenically unsaturated polymerisable group;

b) a cationic monomer of the formula II $$Y^1B^1Q^1 \qquad\qquad II$$

wherein $B^1$ is a bond or a straight or branched alkylene, alkylene-oxa-alkylene or alkylene-oligooxa-alkylene group, any of which optionally includes one or more fluorine substituents;

$Y^1$ is an ethylenically unsaturated polymerisable group; and

Q is an organic group having a cationic or cationisable moiety and C a crosslinkable monomer having the general formula IV:

$$Y^3B^3Q^3 \qquad\qquad IV$$

wherein $B^3$ is a bond or a straight or branched alkylene, alkylene-oxa-alkylene or alkylene-oligooxa-alkylene group, any of which optionally includes one or more fluorine substituents;

$Y^3$ is an ethylenically unsaturated polymerisable group; and $Q^3$ is an organic group having a reactive group capable of cross-linking the polymer.

Preferred reactive comonomers IV which are used to crosslink the comonomer, are those in which $Q^3$ contains a crosslinkable cinnamyl, epoxy, —CHOHCH$_2$Hal (in which Hal is a halogen atom), methylol, reactive silyl, an ethylenically unsaturated crosslinkable group, such as an acetylenic, diacetylenic, vinylic or divinylic group, or an acetoacetoxy or chloroalkyl sulfone, preferably chloroethyl sulphone, group. For optimum cross-linking a monomer including a reactive silyl group (eg a group —SiR$^4{}_3$ in which each $R^4$ is a $C_{1-4}$ alkoxy group or a halogen atom) is used in combination with a is further monomer including a hydroxyl group, eg having the formula IV $$Y^3B^3Q^4 \qquad\qquad IV$$

in which $Y^3$ and $B^3$ are as defined in compound IV and $Q^4$ is a hydroxyl group.

The ethylenically unsaturated monomers from which the polymer is formed may further include a termonomer of the formula III $$Y^2B^2Q^2 \qquad\qquad III$$

wherein $B^2$ is a bond or a straight or branched alkylene, alkylene-oxa-alkylene or alkylene-oligooxa-alkylene group, any of which may optionally include one or more fluorine substituents;

$Y^2$ is an ethylenically unsaturated polymerisable group; and $Q^2$ is an organic group having a hydrophobic group selected from alkyl groups having at least six carbon atoms, fluorine substituted alkyl groups and alkyl groups having at least one siloxane substituent.

For optimum film-forming and ability to coat hydrophobic surfaces, the polymers preferably contain more than 10% by mole, more preferably more than 20% by mole such termonomer.

The polymers may include diluent comonomer. Such diluent comonomer may be used in quantities up to 90 mol %, usually less than 50 mol %. Copolymerisable nonionic monomers may be used such as $C_{1-24}$ alkyl(meth)acrylates, and -(meth)acrylamides, and hydroxy $C_{1-24}$ alkyl(meth) acrylates and -(meth)acrylamides.

In each of the monomers I to IV the ethylenically unsaturated group is preferably selected from CH=CH—($C_6H_4$)—K—, $CH_2$=C(R)C(O)—A—, $CH_2$=C(R)—$CH_2$—O—, $CH_2$=C(R)—$CH_2$OC(O)—, $CH_2$=C(R)OC(O)—, $CH_2$=C(R)O— and $CH_2$=C(R)CH$_2$OC(O)N($R^1$)— wherein:

R is hydrogen or a $C_1$–$C_4$ alkyl group;

A is —O— or —NR$^1$— where $R^1$ is hydrogen or a $C_1$–$C_4$ alkyl group or $R^1$ is —B—X, $B^1Q^1$, $B^2Q^2$ or $B^3Q^3$, as the case may be, where B, $B^1$, $B^2$, $B^3$, $Q^1$, $Q^2$ and $Q^3$ and X are as defined above in the respective one of the formula I to IV and K is a group —(CH$_2$)$_p$OC(O)—, —(CH$_2$)$_p$C(O)O—, —(CH$_2$)$_p$OC(O)O—, —(CH$_2$)$_p$NR$^2$—, —CH$_2$)$_p$NR$^2$C(O)—, —(CH$_2$)$_p$C(O)NR$_2$—, —CH$_2$)$_p$NR$^2$C(O)O—, —(CH$_2$)$_p$OC(O)NR$^2$—, —(CH$_2$)$_p$NR$^2$C(O)NR$^2$—, (in which the groups $R^2$ are the same or different) —(CH$_2$)$_p$O—, —(CH$_2$)$_p$SO$_3$—, or, optionally in combination with B, a valence bond and p is from 1 to 12 and $R^2$ is hydrogen or a $C_1$–$C_4$ alkyl group.

Preferably the ethylenically unsaturated groups of all monomers copolymerised together are either the acrylate type or are the styrene type ($CH_2$=C(R)C(O)A— or CH=CH—($C_6H_4$)—K—), and, most preferably each has the same formula. Preferably the groups A of acrylate type ethylenically unsaturated groups of the zwitterionic, cationic and cross-linkable monomer and any termonomer are the same and are most preferably all —O—.

The zwitterionic group X preferably has a phosphate ester group as the anion or the thioester analogue or amide analogue or a phosphonate. The cationic moiety is preferably a quaternary ammonium group, but may be a sulphonium or phosphonium group. Preferably the cationic group is at the end of the group X distant from the group B.

Preferably X is a group of formula V

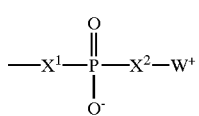

(V)

in which the moieties $X^1$ and $X^2$, which are the same or different, are —O—,—S—, —NH— or a valence bond, preferably —O—, and $W^+$ is a group comprising an ammonium, phosphonium or sulphonium cationic group and a group linking the anionic and cationic moieties which is preferably a $C_{1-12}$-alkylene group.

Preferably W contains as cationic group an ammonium group, more preferably a quaternary ammonium group.

The group $W^+$ may for example be a group of formula —$W^1$—$N^+R^6{}_3$, —$W^1$—$P^+R^7{}_3$, —W—$S^+R^7{}_2$ or —$W^1$—Het$^+$ in which:

$W^1$ is alkylene of 1 or more, preferably 26 carbon atoms optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group $W^1$ optionally contains one or more fluorine substituents and/or one or more functional groups; and either the groups $R^6$ are the same or different and each is hydrogen or alkyl of 1 to 4 carbon atoms, preferably methyl, or aryl, such as phenyl or two of the groups $R^6$ together with the nitrogen atom to which they are attached form a heterocyclic ring containing from 5 to 7 atoms or the three groups $R^6$ together with the nitrogen atom to which they are attached form a fused ring structure containing from 5 to 7 atoms in each ring, and optionally one or more of the groups $R^6$ is substituted by a hydrophilic functional group, and the groups $R^7$ are the same or different and each is $R^6$ or a group $OR^6$, where $R^6$ is as defined above; or Het is an aromatic nitrogen-, phosphorus- or sulphur-, preferably nitrogen-, containing ring, for example pyridine.

Preferably $W^1$ is a straight-chain alkylene group, most preferably 1,2-ethylene.

Preferred groups X of the formula V are groups of formula VI.

The groups of formula (VI) are:

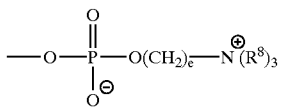

(VI)

where the groups $R^8$ are the same or different and each is hydrogen or $C_{1-4}$ alkyl, and e is from 1 to 6.

Preferably the groups $R^8$ are the same. It is also preferable that at least one of the groups $R^8$ is methyl, and more preferable that the groups $R^8$ are all methyl.

Preferably e is 2 or 3, more preferably 2.

When X is a group of formula (VI) preferably B is a group of formula —(CR$^9_2$)— or —(CR$^9_2$)$_2$—, eg. —CH$_2$— or —(CH$_2$CH$_2$)—.

Preferably the zwitterionic monomer has the general formula VII

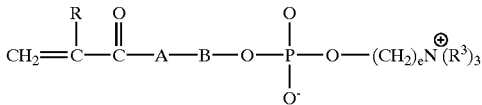

VII wherein R, A and B are defined above, the groups $R^3$ are the same or different and each is hydrogen $C_{1-1}$ alkyl, aryl, alkaryl, aralkyl, or two or three of the groups $R^3$ with the nitrogen atom to which they are attached form a saturated or unsaturated hetero cyclic ring, and e is 1 to 6, preferably 2 to 4.

A cationisable moiety in the group $Q^1$ is generally a group which can easily be protonated to render it cationic, for instance which is protonated in aqueous environments at pH7.

The group $Q^1$ of the cationic monomer is preferably a group $N^+R^5_3$, $P^+R^5_3$ or $S^+R^5_2$ in which the groups $R^5$ are the same or different and are each hydrogen, $C_{1-4}$-alkyl or aryl (preferably phenyl) or two of the groups $R^5$ together with the heteroatom to which they are attached from a saturated or unsaturated heterocyclic ring containing from 5 to 7 atoms. Preferably the group $Q^1$ is permanently cationic, that is each $R^5$ is other than hydrogen. Preferably $Q^1$ is $N^+R^5_3$ in which each $R^5$ is $C_{1-4}$-alkyl, preferably methyl.

The relative ratios (equivalents) of zwitterionic to cationic pendant groups in the molecule of zwitterionic to cationic monomer in the range 1:100 to 100:1 (zwitterionic to ionic) preferably 1:10 to 10:1, more preferably 1:2 to 2:1.

Generally the polymers including the crosslinkable groups are coated onto the stent and crosslinked after coating. Crosslinking is generally by heating, optionally in the presence of moisture, for instance at least 40° C., preferably at least 60° C., for instance around 70° C.

The pharmaceutically active compound may be loaded into the polymer matrix by being co-coated from a composition containing both the compound and cross-linkable polymer. Alternatively, and preferably, the drug is absorbed into or absorbed onto the matrix after the polymer is coated onto the stent and crosslinked thereon. This loading step is carried out by contacting the coated stent, optionally following a pre-swelling step, with a solution or dispersion of the pharmaceutically active compound in a solvent which is capable of penetrating the polymer matrix. Usually the solvent for the pharmaceutical active is a solvent which swells the polymer. Suitable loading compositions comprise water, and may additionally or alternatively comprise an alcohol. The solvent may be removed from the swollen matrix containing pharmaceutical active, but may alternatively be retained in the polymer, for instance during storage or by immediately delivering the stent to the patient.

Loading conditions are determined to achieve adequate loading of active. The temperature is selected so as to create suitable properties on the polymer. It is usually between 0 and 60° C., preferably room temperature to about 40° C., for instance 20 to 40° C., most preferably around 37° C. The solution or dispersion may contain solvents selected so as to achieve appropriate fluidity at the loading temperature.

The stent may be sterilised before or after loading, for instance by gamma-irradiation.

In order to provide adequate loading of drugs, it is preferred for the coating polymer to be at least 0.5 μm, more preferably at least 1 μm, thick (dry thickness). Optionally it is at least 2 μm thick. The polymer coating and the pharmaceutically active compound may be coated only onto the outside of the stent, from which the pharmaceutical active is delivered directly into the wall of the vessel in which the stent is implanted. Preferably, however, the stent is provided with an overall coating of polymer, so that the lumenal surface of the stent is also provided with a coating, which may be thicker or, preferably; is thinner than the external coating.

The stent may be a shape-memory metal stent, a self-expanding stent or a balloon expandable stent. For instance, a self-expanding stent may be a rolled sheet device or a braided device. Most conveniently the stent is an etched tube balloon-expandable stent. The stent may be loaded with drug in the invention when mounted on its delivery device. An overcoat of zwitterionic polymer may be applied over the defined coating to control release in use.

Figure 2:
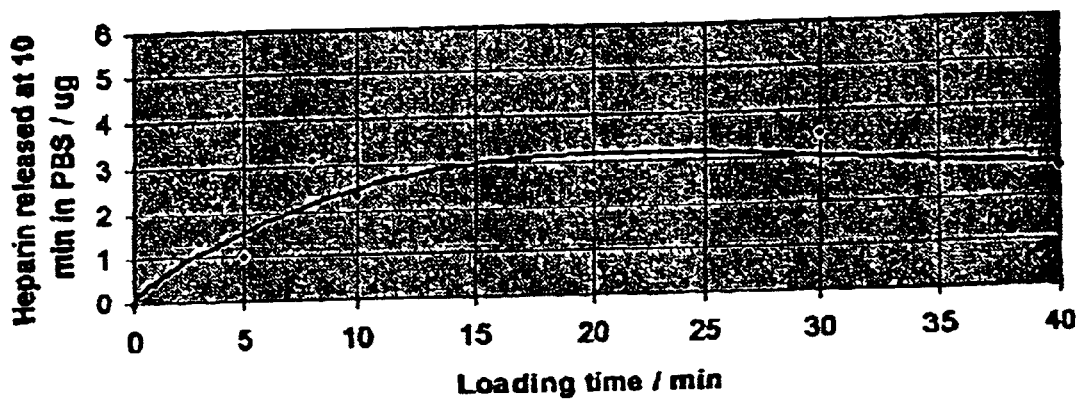
Figure 3:
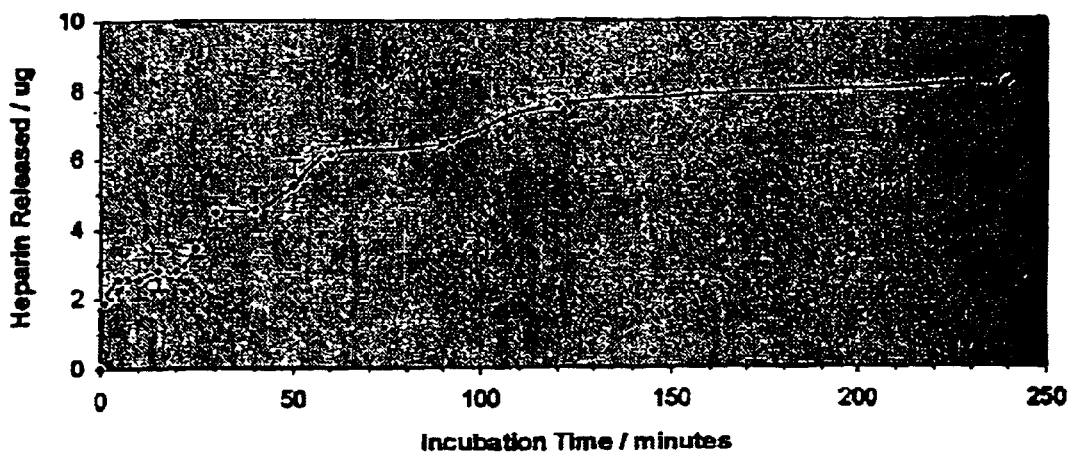
Figure 10:
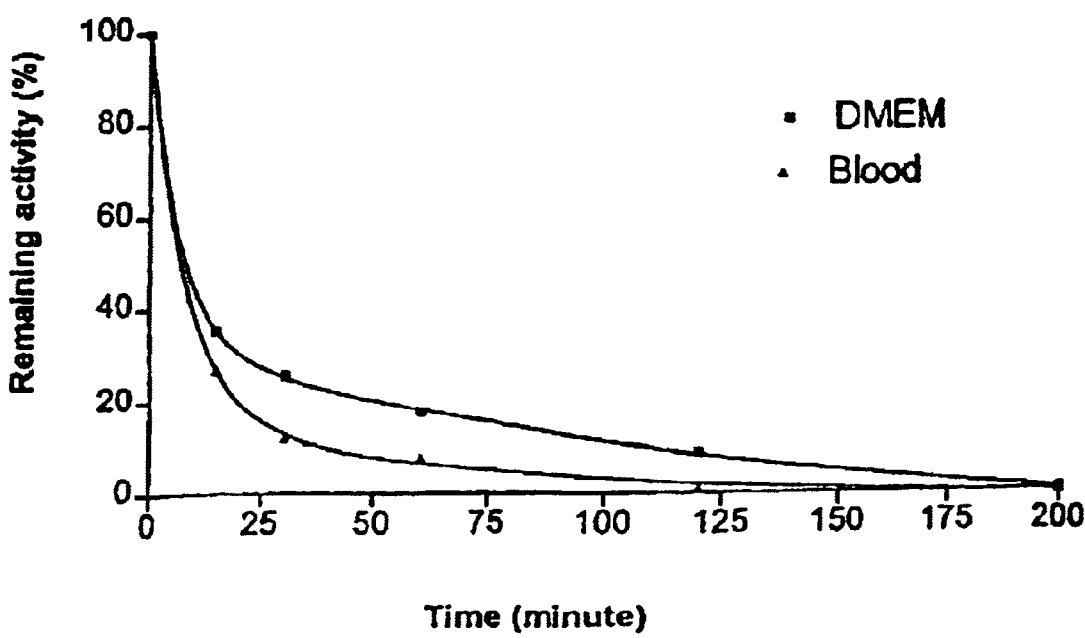
Figure 11:
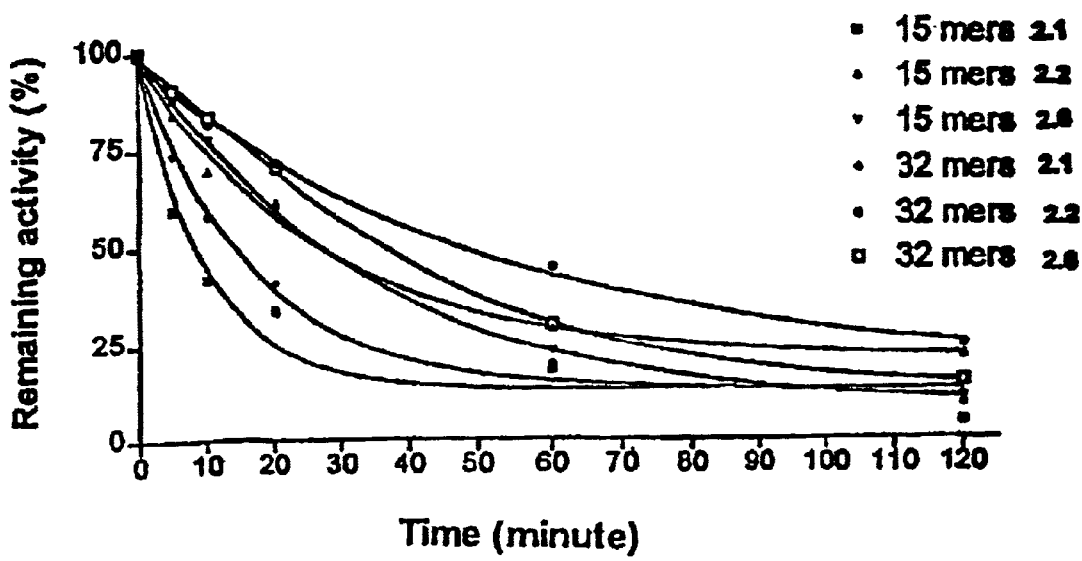
Figure 12:
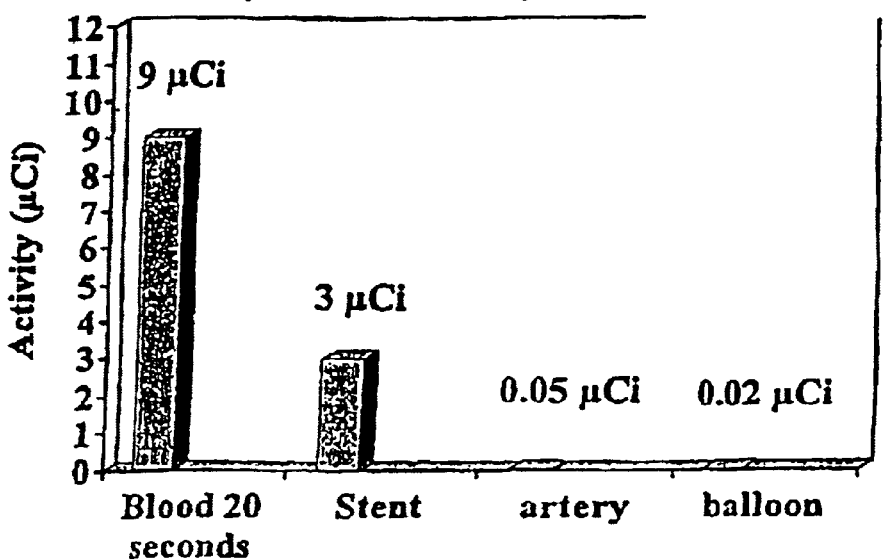
Figure 13:
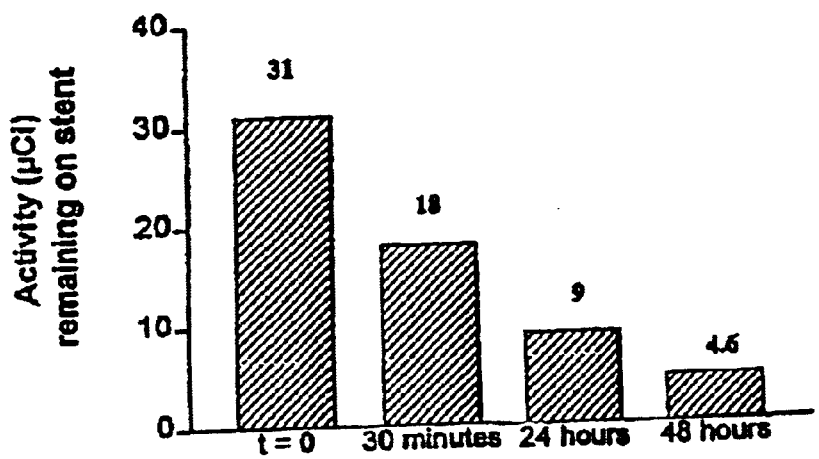
Figure 14:
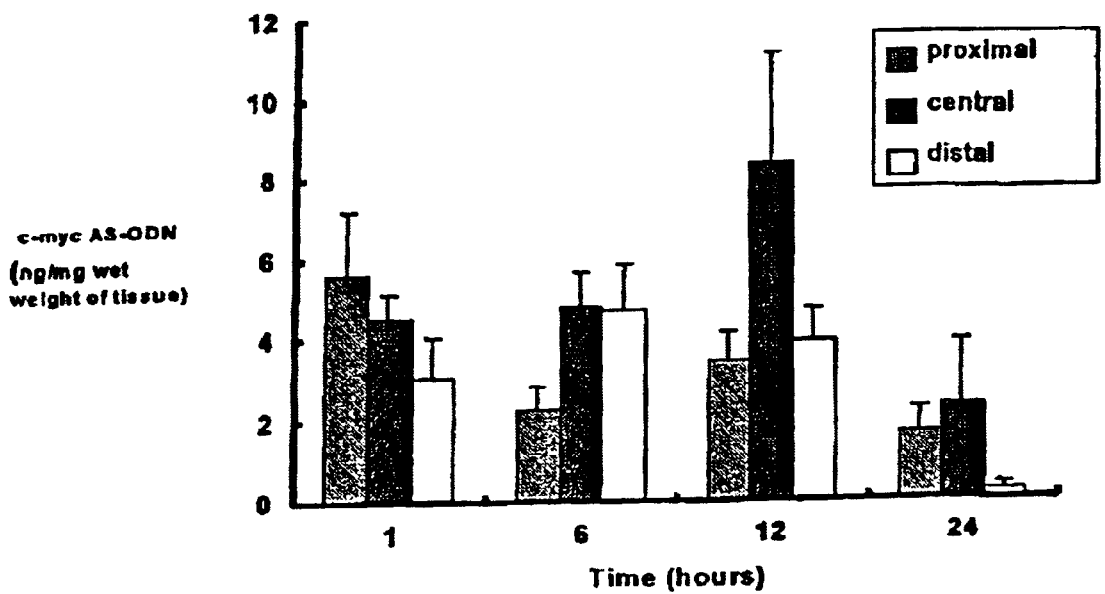
Figure 15:
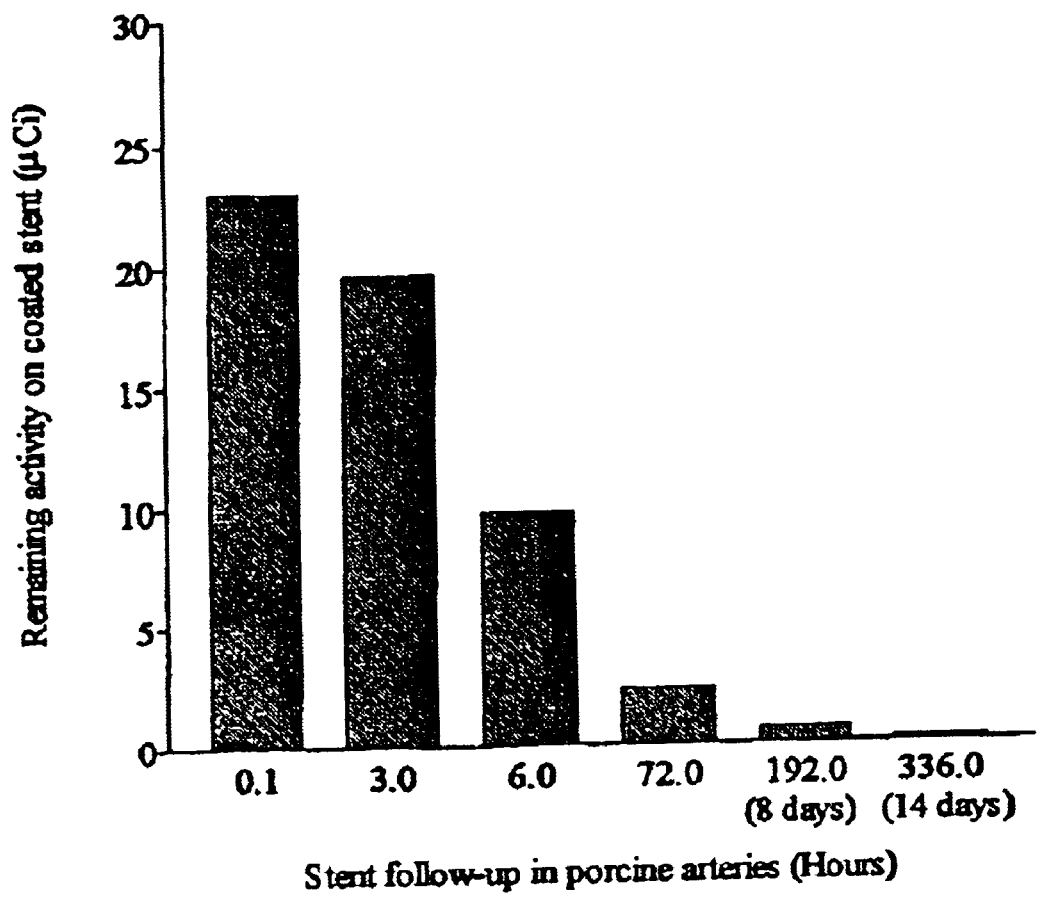
Figure 16:
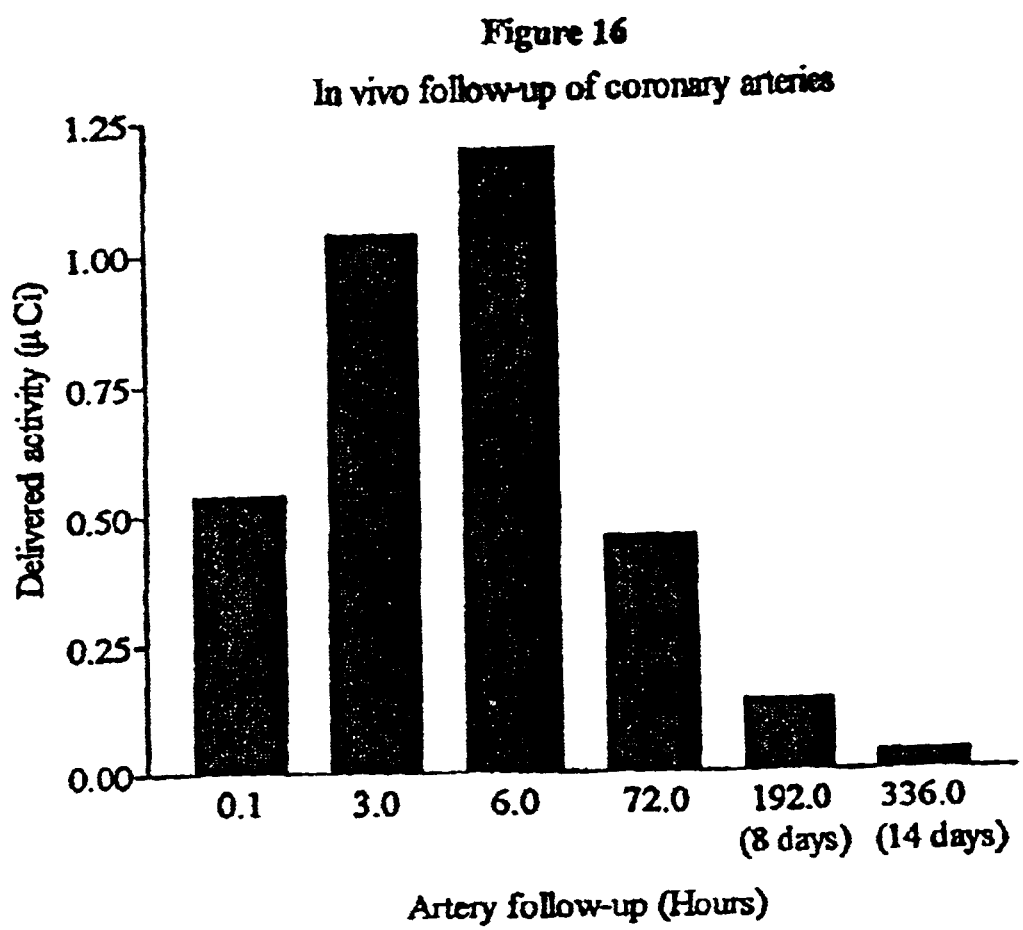
Figure 17:
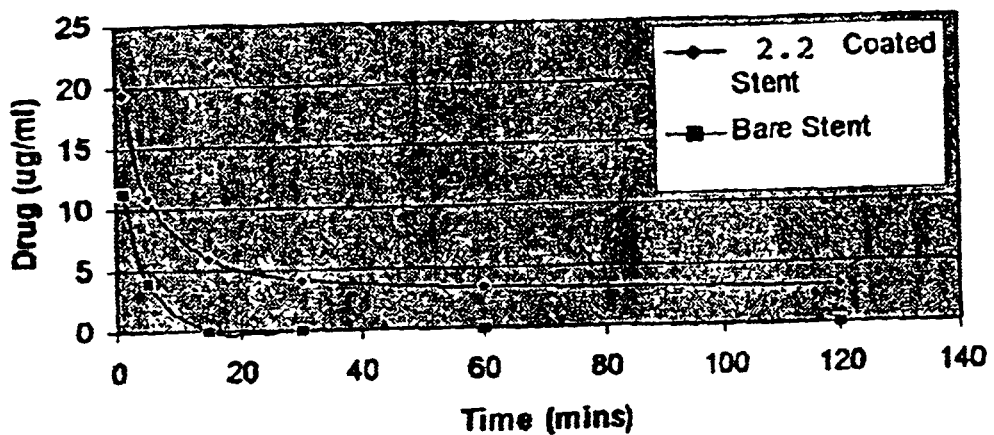
Figure 18:
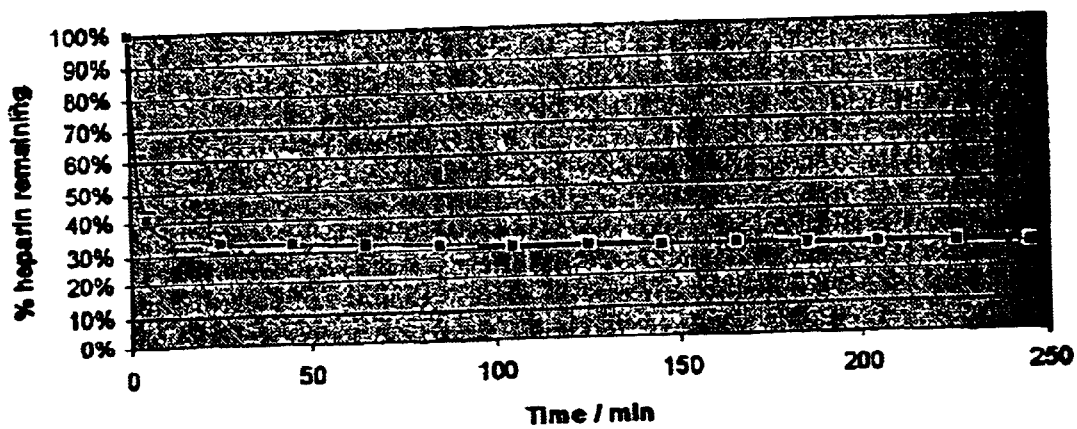
Figure 19:
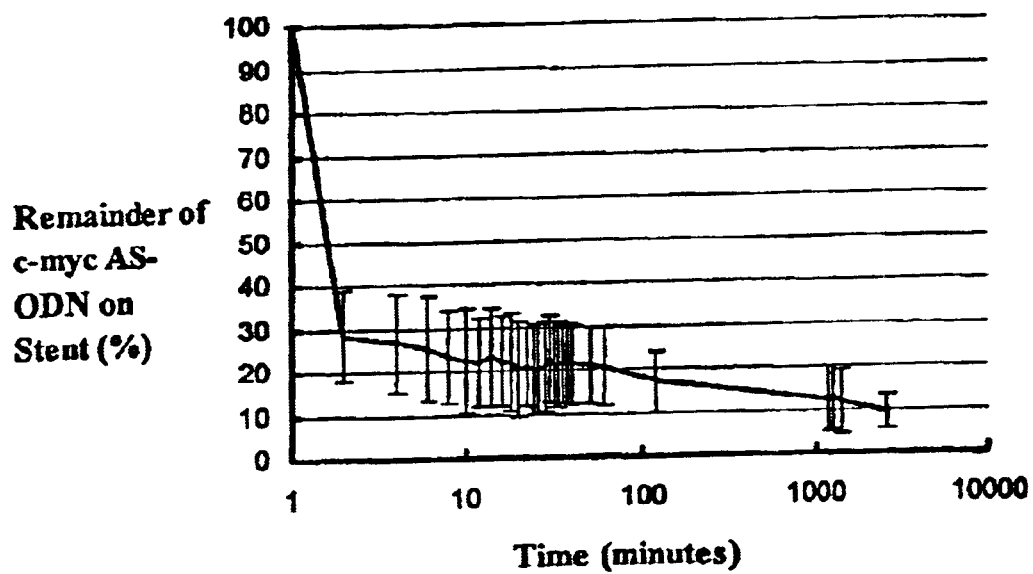
Figure 20:
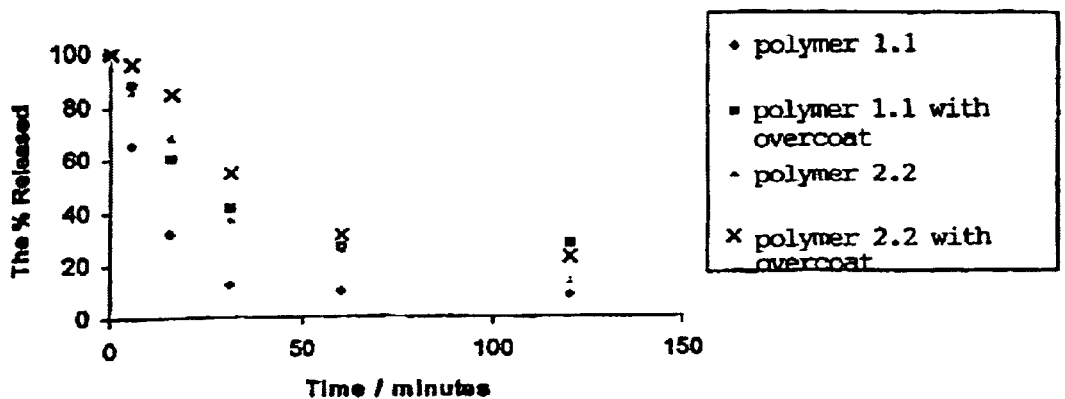
Figure 21:
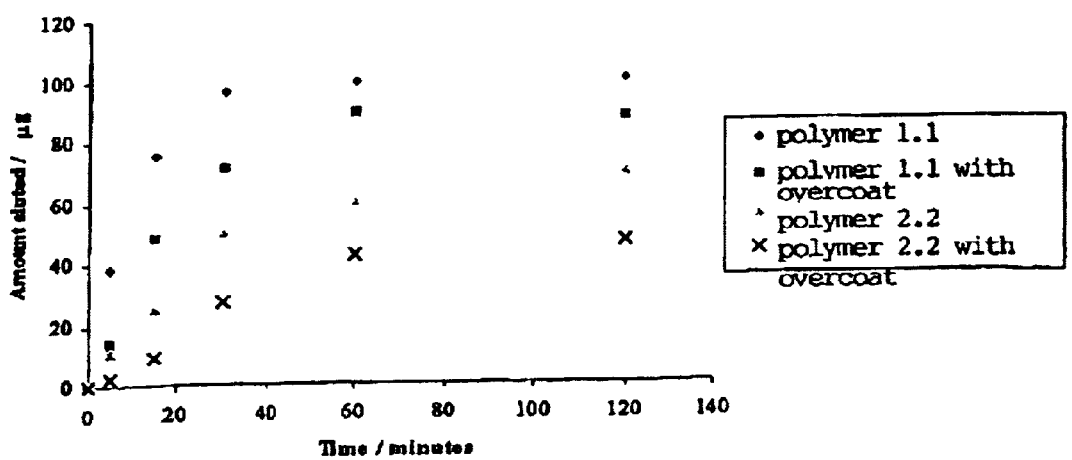
Figure 22:
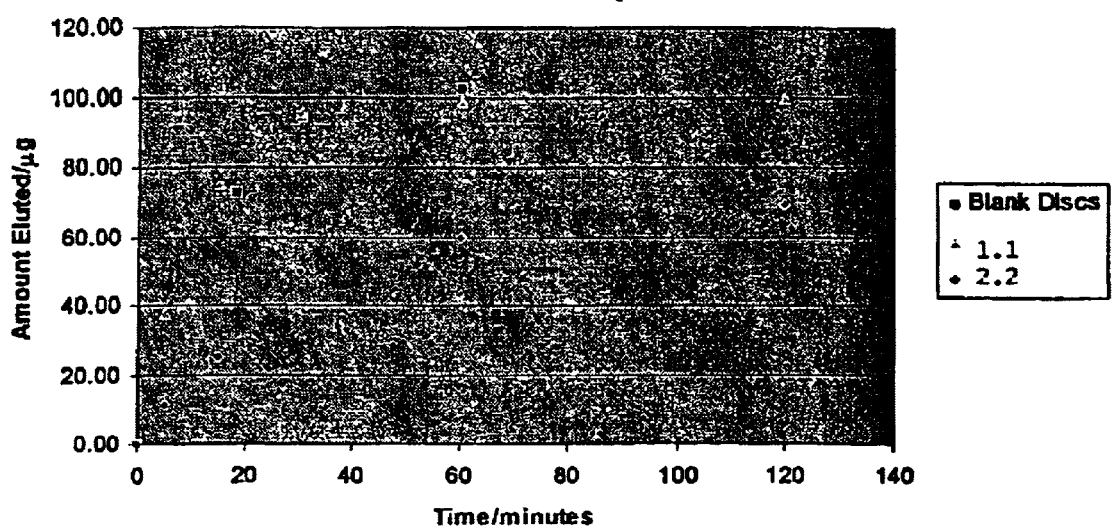

FIG. 1 shows the results of Example 2;
FIGS. 2 and 3 show the results of Example 4a;
FIGS. 4 to 9 show the results of Example 5;
FIGS. 10 and 11 show the results of Example 6; and
FIGS. 12 and 13 show the results of Examples 7a and b;
FIG. 14 shows the results of Example 8b;
FIGS. 15 and 16 show the results of Example 7c;
FIG. 17 shows the results of Example 9;
FIG. 18 shows the results of Example 4b;
FIG. 19 shows the results of Example 8a;
FIGS. 20 to 22 show the results of Example 3.

The following examples illustrate the invention.

Abbreviations

MPC: 2methacryloyloxyethyl-2'-trimethylammonium ethyl phosphate
LM: lauryl methacrylate
HPM: hydroxypropyl methacrylate—(70% 3-hydroxypropyl:30% 2-hydroxy-1-methylethyl)
XL: 3-(trimethoxysilyl)propylmethacrylate
CM: choline methacrylate
DMA: dimethylacrylamide The monomer ratios are on a weight basis based on the amount of monomers used in the polymerisations.

EXAMPLE 1

The objective was to compare the loading of a single stranded oligonucleotide (ASON, c-myc) onto polymer variants to assess the importance of hydrophobicity, hydrophilicity, crosslinking density and level of cationic charge upon the ASON loading of polymer film.

The following drugs/compounds were evaluated and compared:

(i) Antisense—single-stranded oligonucleotide (ASON)
(ii) Dipyridamole—anti-platelet drug
(iii) FITC labelled Dextrans Polymers systems were based upon two types:

| (1) | Reference | |
|---|---|---|
| 1.1 | Polymer of EP 99304140.9 | $MPC_{29}LM_{51}HPM_{15}XL_5$ |
| 1.2 | Hydrophobic variant | $MPC_{15}LM_{65}HPM_{15}XL_5$ |
| 1.3 | Hydrophilic variant | $MPC_{45}LM_{35}HPM_{15}XL_5$ |
| 1.4 | Increased crosslinker | $MPC_{30}LM_{50}HPM_{10}XL_{10}$ |
| 1.5 | Polymer of EP 99304092.2 | $MPC_{37}LM_{63}$ |

| (2) | Invention | |
|---|---|---|
| 2.1 | Standard | $MPC_{29}LM_{50}CM_5HPM_{12}XL_4$ |
| 2.2 | Charge increase | $MPC_{21.5}LM_{42.5}CM_{20}HPM_{12}XL_4$ |
| 2.3 | Hydrophilic variant | $MPC_{48}LM_{30}CM_6HPM_{12}XL_4$ |
| 2.4 | Lower crosslinker | $MPC_{25}LM_{50}CM_6HPM_{14}XL_2$ |
| 2.5 | Hydrophilic polymer | $MPC_{28}LM_{20}CM_6HPM_{12}XL_4DMA_{30}$ |
| 2.6 | High cationic | $MPC_{18}LM_{31}CM_{35}HPM_{12}XL_4$ |

Polymer Preparation

All polymers with the exception of polymer 1.1 were prepared by the pumped feed process as discussed in WO98/22516. The monomers in isopropanol solution, were pumped to a refluxing blend of isopropanol and isopropyl acetate (bp 83° C.), over two hours using AIBN as the initiator.

Coating of Steel Strips

Steel strips (1 cm×1.5 cm) were cleaned in dichloromethane for 10 minutes using the ultra-sonics bath. 200 ul of a 50 mg/ml polymer solution was evenly coated onto the steel strips. For each polymer sample seven steel strips were coated. Coated steel strips were then dried overnight in a oven at 70° C. to cure the polymer films.

Loading of Polymer with Drug

Six of the coated steel strips were placed polymer side down into a well containing a 1 mg/ml drug solution. One control sample was not loaded with drug. The steel strips were submerged for 1 hour. The steel strips were then removed from the well and the excess drug removed by dabbing the surface very gently with tissue. The steel strips were then allowed to dry for a further half hour at room temperature. Each sample was then dipped quickly in clean PBS solution to remove excess drug from the coating. (3 secs dip). Each steel strip was then placed in 3 ml of PBS solution contained in vials. Each vial was then sonicated for 20 mins at a bath temperature of 35° C. in order to extract the drug from the polymer coating. Each solution was then measured using fluorescence spectroscopy to determine the amount of drug uptake Note—In the case of dipyridamole a 50:50 PBS/Ethanol solution was used instead of PBS because of drug solubility. Samples were extracted into a total of 60 ml PBS/Ethanol solution and not 3 ml of PBS in the case of ASON and FTIC-Dextran.

EXAMPLE 1:1

Loading of Polymer Films with ASON

TABLE 1

| Fluorescence readings (Excitation 500 nm Emission 525 nm) | |
|---|---|
| Polymer Type | Drug Uptake ($\mu$g) |
| 1.2 | 0.0 |
| 1.3 | 0.0 |
| 1.1 | 0.0 |
| 1.4 | 0.0 |
| 2.1 | 1.8 |
| 2.2 | 1.6 |

Initial results for 1.1 and 1.2 polymer variants loaded with ASON indicated that polymer 1.1 does not take up any ASON whilst polymer 2.1 takes up a small quantity of the drug. The loading of ASON into polymer 2.1 would first appear to be associated with the presence of a charge on the polymer. The results also show that when the charge level is increased the polymer coating does not seem to take up further amounts of drug. The main benefit of charge increase is to slow down the release rate of active compound (ASON).

The uptake of ASON in polymer 2.1 may be due to the interactions of the negative charge associated with the ASON molecule and the positive charge associated with the presence of Cm in the polymer coating.

Samples 2.1 and 2.2 were subjected to a further one-hour sonication to determine if any more ASON was released. The results showed no difference to those observed after 20 minutes indicating that 1.6 and 1.8 ug was probably the total loading.

EXAMPLE 1:2

Further work was carried out to investigate if the ASON molecule was too large to penetrate into the polymer coatings by assessing drug uptake vs film thickness. The aim of the experiment was to indicate if ASON penetration of the polymer had occurred.

Steel strips were coated with various amounts of 2.1 and 1.1 polymer at 200, 500, and 800 ul of a 50 mg/ml polymer stock solution. Each steel strip was then loaded with ASON by the method previously described. The results obtained are shown in Table 2.

TABLE 2

| Polymer Type | Polymer Quantity µl | Drug Uptake (µg) |
|---|---|---|
| 1.1 | 200 | 0.0 |
| 1.1 | 500 | 0.0 |
| 1.1 | 800 | 0.0 |
| 2.1 | 200 | 3.8 |
| 2.1 | 500 | 6.3 |
| 2.1 | 800 | 9.8 |

Results showed that the polymer with no overall charge does not appear to absorb ASON whereas the cationic polymer does. It would appear that the uptake of drug in the case of the cationic polymer is related to the polymer volume not just surface area.

EXAMPLE 1:3

The observations so far have indicated that ASON was only absorbed by cationic type polymers. The next approach was to study the effects of hydrophobicity, hydrophilicity and crosslinking densities of such polymers to determine if changes in the polymer network would increase the loading of the ASON. The results obtained for 200 ul coatings are shown in Table 3.

TABLE 3

| Polymer Type | Drug Uptake (µg) |
|---|---|
| 2.3 | 2.4 |
| 2.4 | 8.3 |
| 2.5 | 0.0 |
| 2.1 | 5.4 |

The results obtained confirmed previous findings in that the cationic polymer does absorb ASON but that changes in polymer composition do not seem to increase the degree of uptake in the polymer coating with the exception of a lower crosslinking polymer system. The hydrophilic copolymer may not be optimised in terms of coating property, resulting in its apparent failure to absorb drug.

EXAMPLE 1:4

Effect of Drug Molecular Weight on the Amount Loaded

In order to study the effect of drug molecular weight on the amount loaded into a polymer coating, a compound with a variety of molecular weights which could be detected by fluorescence had to be identified. One such compound was Fluorescein Iso Thiocyanate Dextran (FITC-Dextran). This is a neutral compound.

FITC-Dextran is a simple polysaccharide and is available in a range of molecular weights i.e. 4400D, 9500D, 19500D, 42000D, and 77000D. The size of these compounds are similar to ASON which has a molecular weight of 5000D.

The experiment indicated that the FITC-Dextran (mwt 4400) could not be detected in either polymer coatings. This observation that polymer 2.1 does not absorb any dextran, indicates the importance and requirement of a negative charge on the molecule for uptake into and onto the polymer 2.1 coating. As previously seen polymer 1.1 does not take up compounds/drugs with molecular weights >4400D.

EXAMPLE 2

Double Stranded Oligonucleotides (DSON) (Mol wt 1000D)

BiodivYsio stents were coated on the automated stent coating rig, which dips and removes the stent into the solution several times with intermediate drying, using the following conditions.

| | |
|---|---|
| Polymer | 25 mg/ml in ethanol |
| Number of dips | x5 |
| Air pressure (vacuum) | 6 bar |
| Dip speed | 5 mm/s (25 V on power pack) |
| Drying time under vacuum | 2 minutes per dip cycle |
| Stents were then cured at 70° C. overnight. | |

Loading Studies

The stents were loaded with DSON. By immersion in a well containing DSON at a concentration of 1 mg/ml in phosphate buffered saline (PBS). Each stent was loaded for 1 hour. Once the loading was complete the stent was removed from the well and the excess DSON removed by dabbing the stent very gently with tissue.

The stents were placed in PBS (2 ml) and sonicated for 1 hour to remove the absorbed/adsorbed DSON from the stents. Two methods were used to confirm the quantity of material loaded.

(1) Fluorescence (Ex500 nm/Em525 nm)

Total Drug Loading 2 mg/ml Solution (DSON in Water): 4 µg 1 mg/ml Solution (DSON in Water/PBS 50:50): 5 µg Repeat study—1 mg/ml Solution (DSON in Water/PBS 50:50): 6 µg (2) UV (@258 nm)

Total Drug Loading 1 mg/ml Solution (DSON in PBS): 16 µg (before filtration)

1 mg/ml Solution (DSON in PBS): 12 µg (after filtration)

The values obtained for the total loading were obtained after placing the loaded stent into a sonication bath for about an hour. Results do indicate that upon sonication some of the polymer coating may be removed from the stent and thus may give rise to much larger values than one would expect, hence it was felt necessary to filter the solutions before analysis. The graph in FIG. 1 shows release of oligonucleotides from PC Coated BiodivYsio Stents.

The BiodivYsio stents were loaded with ASON and DSON from a 1 mg/ml in PBS (50:50 water:PBS). The uptake onto a 15 mm BiodivYiso Stent coated with polymer 2.1 at approx 1–2 µm was:

ASON—5.3 µg (10 mg/ml-52 µg)

DSON—5–110 µg

The elution into PBS was determined as shown above.

This study investigating the loading and release of ASON was repeated using gamma irradiated polymer 2.1 coated 15 mm BiodivYsio stents. The results were the same as for the non-gamma irradiated polymer coated stents This indicates that there is no change in the ability of the polymer to absorb/adsorb compounds after irradiation.

EXAMPLE 3

Plasmid DNA

The aim of this study plan was to determine the loading and drug release profiles of plasmid DNA (MW about 50 kDa) from polymer coated discs.

Steel discs were cut with a diameter of 13 mm. Each disc was thoroughly cleaned. The discs were then dried in air for 2 hours. A volume of 20 µl of polymer 2.2 or 1.1 coating solution (15 mgml$^{-1}$) was added to one side of each disc and allowed to dry for 2 hours. The reverse side of each disc was then coated in the same way. The coated discs were thermally cross-linked at 70° C. for 4 hours. Additionally steel discs with no coating were studied for comparison.

A volume of 20 µl DNA-plasmid solution (2.325 µg/µl) was added to one side of each disc. The discs were allowed to dry for 3 hours. This procedure was repeated on the other side.

Some of the discs were overcoated. This was carried out by spray coating the polymer coated and loaded discs with a 20 mg/ml solution of polymer 1.5 in ethanol.

The loaded discs were placed in 2 ml of PBS. After a given period of time 1 ml of the solution was withdrawn and placed into a plastic vial. The 1 ml of solution was replaced with 1 ml of fresh PBS. This procedure was repeated at different time intervals. The DNA is quantified using a uv/vis spectrophoto meter. The release data are represented graphically (see FIGS. 20–22). FIG. 20 shows the release of the DNA-plasmid from the two coatings both with and without overcoating. The data is expressed in terms of percentage lost overtime. Approximately 90–100 µg of DNA-plasmid was loaded onto each disc. FIG. 21 again shows the release of the DNA-plasmid from the two coatings both with and without overcoating. The data is expressed in terms of actual amounts of DNA-plasmid lost from the disc. FIG. 22 shows similar results but shows the release from uncoated steel discs compared to polymer coated discs.

The DNA-plasmid seems to release more slowly from the cationic polymer coating 2.2, than the neutral coating (polymer 1.1). There seems to be a significant amount of DNA-plasmid on the polymer 2.2 coating after 60 minutes with the very little remaining on the polymer 1.1 coating after this time.

On the polymer 2.2 coated steel discs there is a significant amount of DNA-plasmid remaining after several hours-which is probably material which interacts strongly with the positively charged surface. There is little difference between the rate and overall elution from the polymer 1.1 coating compared to uncoated steel discs. The overcoating of the plasmid reduces the overall rate of elution for both polymer types.

EXAMPLE 4

Heparin Loading and Release Using Coated BiodivYsio Stents a) Polymer 2.1 Coated Stents This study investigated the ability of polymer 2.1 coated stents to take up and release a sample of unfractionated heparin with an average molecular weight of approx. 10000D.

Loading was carried out by immersion of the coated stents into a solution of heparin in PBS. A range of conditions were used to investigate the loading onto the stents.

TABLE 4

| Heparin concentration for loading/mg ml$^{-1}$ | Loading time/ min | Volume of PBS for releasing | Tmax/* min | Wmax/** µg | Total loading/ µg |
| --- | --- | --- | --- | --- | --- |
| 0.2 | 30 | 1 | 15 | 0.73 | 3.4 |
| 2.0 | 30 | 0.5 | 20 | 2.07 | N/A |
| 10 | 5 | 0.5 | 10 | 13.93 | N/A |

Table 6 Summary of conditions and results of heparin loading and release Notes—*the time where released heparin reaches maximum; **the maximum weight of heparin released during a releasing experiment (see maximum point of the release profile, FIG. 2)

FIG. 2 Effect of loading time on the amount of heparin loaded.

FIG. 3 Heparin release profile of a stent loaded with 2 mg/ml heparin for 4 hours.

The results from the heparin study indicate that as expected it can be adsorbed/absorbed onto the polymer 2.1 coated stents and that it is released from the stents over a prolonged period of time.

b) Polymer 2.2 Coated Stents

Radiolabelled ($^{35}$S) heparin (MW 8–10 kDa) was loaded onto stents coated with polymer 2.2, from a 2 mg/ml aqueous solution. To determine the total loading the stents were placed into liquid scintillant and coated for radioactivity. The mean uptake of heparin was 11 µg per stent. The stents were each placed into a volume of PBS to determine the rate of elution of heparin over a 4 hour period. The results, reported in terms of percentage of heparin remaining in the stent, are shown in FIG. 18. The results show that heparin is released initially as a burst, probably due to immediate wash off of loosely associated heparin, followed by a slow release phase. Extrapolation of the release data indicates that 100% of the heparin is likely to take place after about 24 hours.

EXAMPLE 5

Effect of Time, Temperature and of Oligomer Size and Cationic Content of Polymer During Loading on Loading Levels The purpose of this study was to examine the feasibility of loading short DNA oligonucleotides onto 15 mm PC coated BiodivYsio Drug Delivery stents and optimize the various parameters that may influence drug loading. We loaded 15 mer and 32-mer $^{32}$P radio labelled single stranded DNA oligonucleotides from a 300 ul solution onto PC coated stents (using polymers 2.1, 2.2 and 2.6 described above) using various conditions. We examined the effects of temperature (23, 37, 45, 65° C.), exposure time to drug solution (5, 10, 20, 30 minutes), drug activity (concentration) (11–500 uCi/300 ul) and cationic monomer content in the polymer (5, 20 and 35 weight %). Total loading was assessed in a scintillation counter. All loading experiments were successful.

Figure 4:
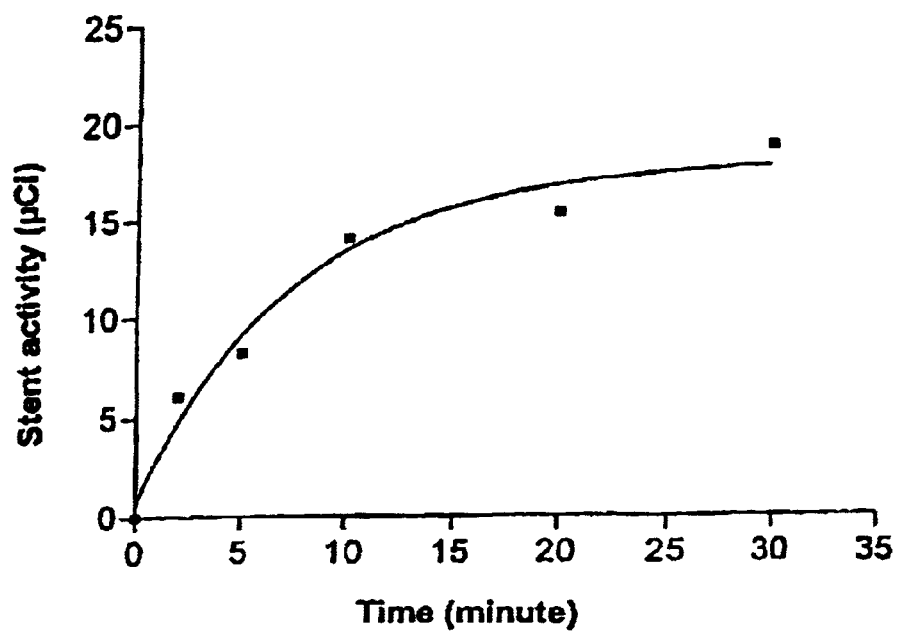

The effect of exposure time on loading levels for the 15 mer loaded at 37° C. onto the stent coated with polymer 2.1 is shown in FIG. 4.

Figure 5:
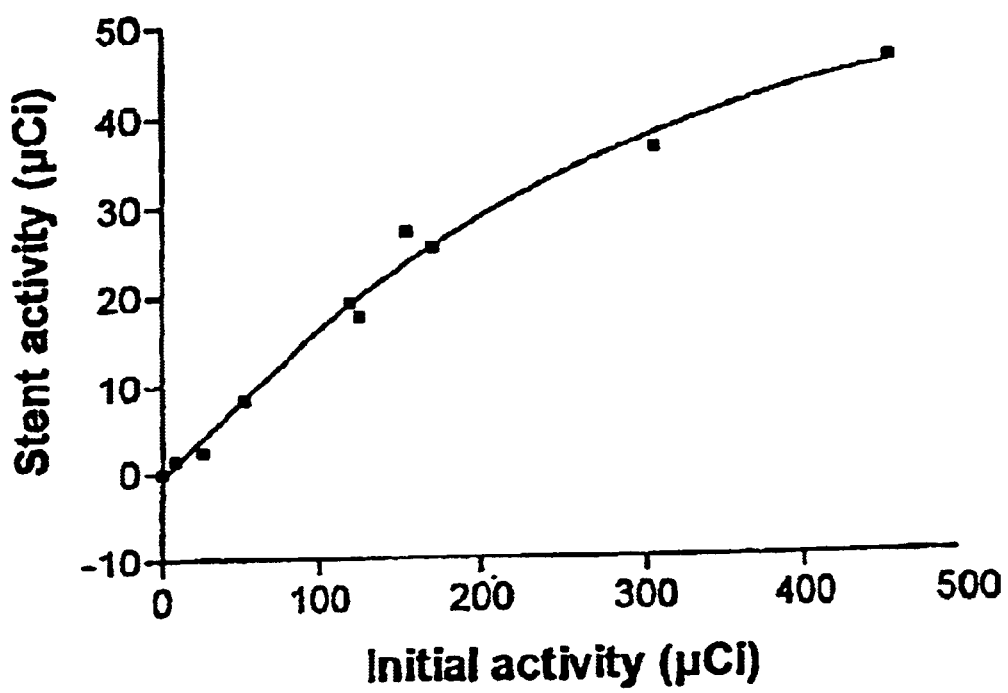

The effect of changing the concentration of 15-mer in the loading solution on loading levels (using polymer 2.1, a coating time of 30 mins and a temperature of 37° C.) is shown in FIG. 5.

Figure 6:
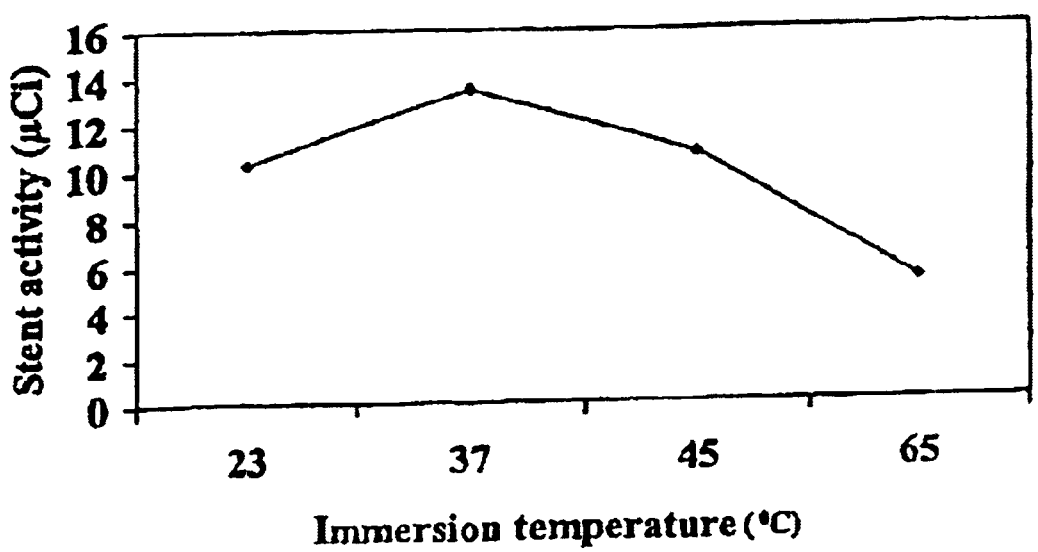

The effect of changing the temperature of the drug solution on loading levels (using polymer 2.1, a coating time of 30 mins and a 15 mer concentration of 75 µCi) is shown in FIG. 6.

Figure 7:
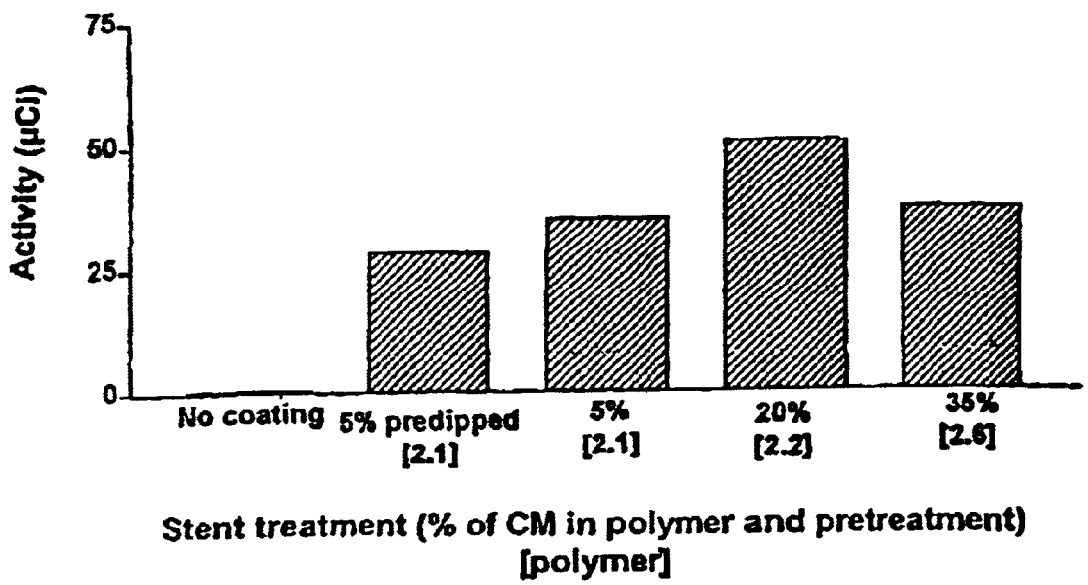
Figure 8:
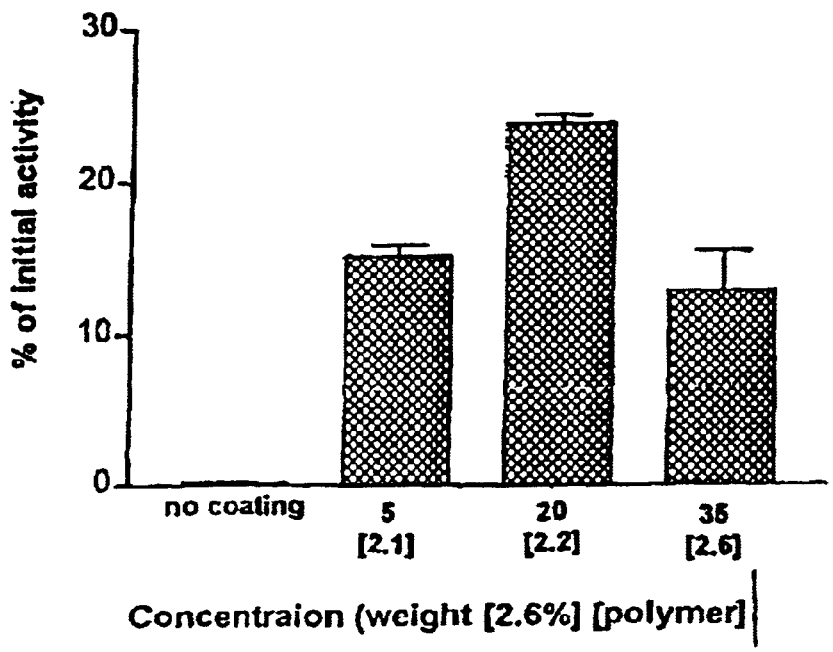
Figure 9:
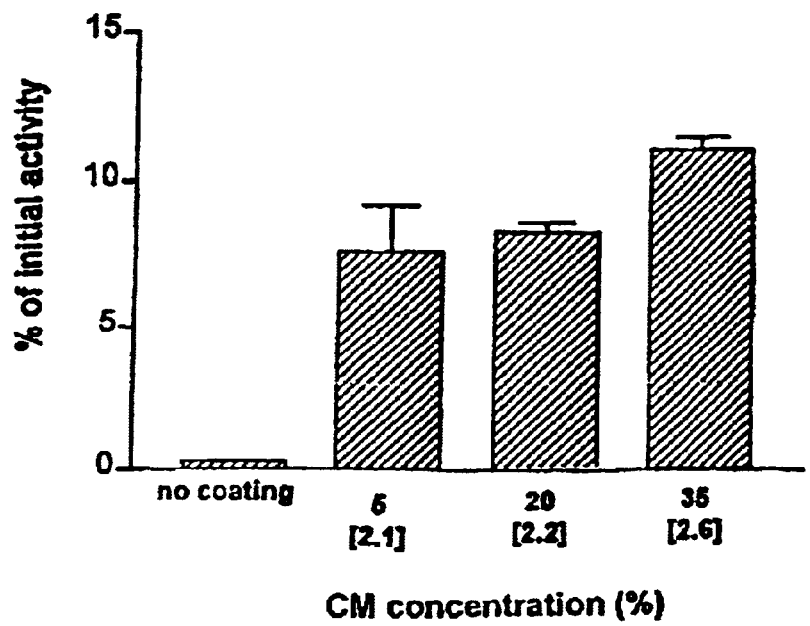

The effect of changing the level of cationic monomer in the polymer and of pre-soaking the coating with deionised water for one hour on loading levels (using a coating time of 30 mins and at a temperature of 37° C. with drug at an initial concentration of 211 µCi in 300 µl for both 15 mer and 32 mer oligonucleotides) is shown in FIGS. 7 to 9.

Maximal loading was obtained at 37° C. (p,0.05), with plateau in total drug loading attained after 10 minutes of stent exposure to the solution. Efficiency of loading was 10% using these parameters. Optimal loading was realised with increasing drug concentration, with 45.8 µCi (3.27 ug DNA) loaded using a 458 µCi (34 µg DNA) solution. Also, increasing CM content of the polymer on the stent to 20% improved maximal loading when compared to other concentrations (p<0.05 vs.0 and 6%).

EXAMPLE 6

Elution of Oligonucleotides from Stents in vitro

Stents coated with polymers 2.1, 2.2 and 2.6 and loaded with 15 mer or 32 mer $^{32}$P labelled oligomers (37° C., 30 mins, with or without presoak in deionised water, at 211 µCi in 300 µl concentration in the soaking solution), were incubated in either human blood or DMEM cell culture medium at 37° C. Samples of the incubation medium were taken over a period and evaluated for radioactivity. The results were used to calculate the % oligomer remaining on the stent after periods of time.

FIG. 10 shows the elution profile for 15 mer from stents coated with polymer 2.1 incubated in blood and cell culture medium.

FIG. 11 shows the elution profiles for 15 mer and 32 mer from stents coated with the different polymers and for polymer 2.1 presoaked in deionised water, upon incubation with blood.

EXAMPLE 7

Release of Oligomer in vivo a) Stents (15 mm×3.5 mm) coated with polymer 2.1 were loaded with $^{32}$p labelled 15 mer ATGCCCCTCAACGTG (sequence ID 1) at a total label loading of 12 µCi per stent. A loaded stent was then deployed into the LCX artery of a pig. The pig was sacrificed after 30 mins. A blood sample was taken, the stent retrieved the level of 15 mer determined for the blood, stent, artery wall and balloon. The results are shown in FIG. 12.

b) A similar experiment was conducted but using 32 mer at a higher loading, on stent coated with polymer 2.2. Blood samples were taken at zero time, 30 minutes after deployment, 24 hours and at sacrifice at 48 hours. The results are shown in FIG. 13.

c) Stents coated with polymer 2.1 and loaded with the same $^{32}$p labelled 32-mer as used in experiment 8c) were mounted on balloon catheters and delivered into a porcine carotid arteries in vivo. 2-to 3 animals were used for each time point viz. 0, 3.6 and 72 hours and 8 and 14 days. At the specified time point after delivery the level of $^{32}$P label remaining on the stent and the tissue uptake of the oligonucleotide from the stent into artery and myocardium was measured by scintillation counting.

The results are shown in FIGS. 15 and 16.

Conclusions

The results of examples 7a)–c) show that oligonucleotides are released in vivo into the vessel wall surrounding the stent, with little detected in the tissue adjacent to the vessel in which the stent is implanted. Thus, in example 7c) there was very little radioactivity detected in the myocardium. The efficiency of delivery is much higher than using a local drug delivery catheter, the infiltrator (TM). Comparative results show that delivering a dose of 1680 µCi $^{32}$p labelled ODN results in the same level of label in the tissue at 3 and 6 hours as a dose of only 100 µG from a stent. Lower doses of these compounds may be used to delivery to target tissue.

EXAMPLE 8

Fluorescence Labelled Oligonucleotide a) Uptake and Release on Polymer 2.2 Coated Stent Stents coated with polymer 2.2 were loaded with a 15-mer c-myc antisense oligonucleotide AACGTTGAGGGGCAT (sequence ID 2) labelled with a fluorescence label by immersing them for 30 minutes in a 5 mg/ml solution of the DNA in physiological saline.

The total loading was determined by placing 3 of the stents each into 3 ml PBS and sonicating for 30 minutes. The fluorescent label was quantified. The loading was found to be about 20 µg per stent. Release into PBS is shown in FIG. 19.

b) Release and Uptake in Porcine Carotid Artery.

Polymer 2.1-coated stents were loaded with the same oligonucleotide used in 8a. The stents were wick dried. Each stent was deployed in a 50 mm long section of poveine carotid artery by mounting on a balloon and inflation of the balloon in the section. The section of artery as then mounted onto cannulae in a chamber filled with culture medium. Further culture medium was coused to flow through a circuit of silicone tubing and thence through the section of artery at a rate of 60 ml min$^{-1}$. After 1, 6, 12 or 24 hours the stented section was removed from the circuit and the ends of the vessel proximal and distal from the stent removed for qualification of ODN. The stented segment of vessel was gently pulled away from the stent. All three vessel segments were snap frozen in liquid nitrogen, pulverised and incubated one night in lysis buffer. Following sonication and centrifugation the supernatants were measured for fluorescence to determine the concentration of label, presumed to remain associated with ODN. The results are shown in FIG. 14. The level of fluorescence label in the circulating liquid was detected at the end of each experiment and found to be below the level of detection of the reader. One of the started sections of vessel was instead of being analysed for the total fluorescence label, sectioned and observed under confocal microscopy after ethidium bromide staining. The results show that oligonucleotide costains with ethidium bromide believed to indicate a nuclear location.

EXAMPLE 9

Abcixmab Loading and Elution in vitro

Abcixmab is an antibody (MW about 50 kDa) to glycoprotein IIb/IIIa, administered systemically prior to and following stenting to minimise thrombus formation. Abcixmab potentially reacts with the aVβ3 present on smooth muscle cells and responsible for mediating smooth muscle cell migration, thereby influencing restenosis beneficially. It has an overall anionic charge.

In this study $^{125}$I-labelled abciximab was loaded onto stents coated with either polymer 2.2 or as a comparison a bare stent (no polymer) by immersing the stents in a solution of 2 mg/ml drug in phosphate buffered saline containing 0.001% polysorbate 80 to assist dissolution for 30 minutes at room temperature. The stents were removed and wick dried. The stents were then placed into channels each forming part of a separate circuit of recirculating (20 m/min) phosphate buffered saline containing 1% albumin at 37° C. The level of 1251 label remaining on the stent was determined by measuring the level of label in the circulating PBS over a period of 24 or 48 hours and reported in percentage terms. The results are shown in FIG. 17. The total loading of drug on stent was also determined and found to be about 5 µg per stent for the stents coated with polymer 2.2.

The results show that the active is released over a more extended time from the cationic polymer than from the bare stent.

What is claimed is:

1. An implant having a coating on its external surface comprising:
   a) a crosslinked, water swellable polymer matrix having a dry thickness of at least 0.1 μm, and
   b) a pharmaceutically active compound comprising a nucleic acid, in which the polymer has pendant zwitterionic groups and pendant cationic groups.

2. An implant having a coating on its external surface comprising:
   a) a crosslinked, biostable polymer matrix and
   b) a pharmaceutically active compound which is a nucleic acid, in which the polymer has pendant zwitterionic groups and pendant cationic groups.

3. An implant having a coating on its external surface comprising:
   a) a cross-linked, biostable polymer and
   b) a pharmaceutically active compound which is a protein which is anionically charged at physiological pH in which the polymer has pendant zwitterionic groups and pendant cationic groups.

4. An implant according to claim 3 which the protein is an antibody or fragment thereof.

5. An implant according to claim 1 which the polymer is formed from ethylenically unsaturated monomers including less than 20 mole % cross-linkable monomer.

6. An implant according to claim 1 in which the polymer is formed from ethylenically unsaturated monomers including
   a) a zwitterionic monomer of the formula I

YBX      I wherein B is a bond or a straight or branched alkylene, alkylene-oxa-alkylene or alkylene-oligooxa-alkylene group, any of which optionally include one or more fluorine substituents;
   X is an organic group having a zwitterionic moiety; and
   Y is an ethylenically unsaturated polymerisable group;
   b) a cationic monomer of the formula II $Y^1B^1Q^1$      II wherein $B^1$ is a bond or a straight or branched alkylene, alkylene-oxa-alkylene or alkylene-oligooxa-alkylene group, any of which optionally includes one or more fluorine substituents;
   $Y^1$ is an ethylenically unsaturated polymerisable group; and
   Q is an organic group having a cationic or cationisable moiety and
   c) a crosslinkable monomer having the general formula IV:

$Y^3B^3Q^3$      IV wherein $B^3$ is a bond or a straight or branched alkylene, alkylene-oxa-alkylene or alkylene-oligooxa-alkylene group, any of which optionally includes one or more fluorine substituents;
   $Y^3$ is an ethylenically unsaturated polymerisable group; and
   $Q^3$ is an organic group having a reactive group capable of cross-linking the polymer.

7. An implant according to claim 6 in which $Q^3$ contains a crosslinkable moiety selected from the group consisting of cinnamyl, epoxy, —CHOHCH$_2$Hal in which Hal is a halogen atom, methylol, reactive silyl, ethylenically unsaturated, acetoacetoxy and chloroalkyl sulfone groups.

8. An implant according to claim 7 in which $Q^3$ is a group $SiR^4_3$ in which each $R^4$ is a $C_{1-4}$ alkoxy group or a halogen atom.

9. An implant according to claim 8 in which the monomers further include a compound of the formula IV'

$Y^3B^3Q^4$      IV' wherein $B^3$ is a bond or a straight or branched alkylene, alkylene-oxa-alkylene or alkylene-oligooxa-alkylene group, any of which optionally includes one or more fluorine substituents;
   $Y^3$ is an ethylenically unsaturated polymerisable group and $Q^4$ is a hydroxyl group.

10. An implant according to claim 6 in which X is a group of formula V

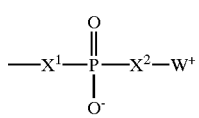

(V)

in which the moieties $X^1$ and $X^2$, which are the same or different, are selected from the group consisting of —O—, —S—, —NH— and a valence bond, and $W^+$ is a group comprising a cationic moiety selected from the group consisting of ammonium, phosphonium and sulphonium groups and a group linked to $X^2$ which is a $C_{1-12}$ alkylene group.

11. An implant according to claim 10 in which the groups Y, $Y^1$ and $Y^3$ all have the general formula $CH_2=C(R)C(O)$A— in which A is —O— or —$NR^1$ where $R^1$ is hydrogen or a $C_{1-4}$ alkyl group, and R is hydrogen or a $C_{1-4}$ alkyl group.

12. An implant according to claim 11 in which $W^1$ is 1,2-ethylene.

13. An implant according to claim 10 in which X is a group of formula VI

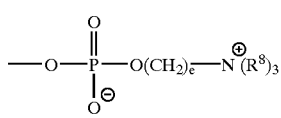

(VI)

where the groups $R^8$ are the same or different and each is hydrogen or $C_{1-4}$ alkyl, and e is from 1 to 6.

14. An implant according to claim 1 in which $Q^1$ is selected from the group consisting of $N^+R^5_3$, $P^+R^5_3$ and $S^+R^5_2$
   in which the groups $R^5$ are the same or different and are each selected from the group consisting of hydrogen, $C_{1-4}$-alkyl and aryl, or two of the groups $R^5$ together with the heteroatom to which they are attached form a saturated or unsaturated heterocyclic ring containing from 5 to 7 atoms.

15. An implant according to claim 1 in which the monomers further include a termonomer of the formula III $Y^2B^2Q^2$      III wherein $B^2$ is a bond or a straight or branched alkylene, alkylene-oxa-alkylene or alkylene-oligooxa-alkylene group, any of which may optionally include one or more fluorine substituents;

$Y^2$ is an ethylenically unsaturated polymerisable group; and $Q^2$ is an organic group having a hydrophobic group selected from alkyl groups having at least six carbon atoms, fluorine substituted alkyl groups and alkyl groups having at least one siloxane substituent.

16. An implant according to claim 15 in which $Y^2$ is selected from the group consisting of CH=CH—($C_6H_4$)—K—, $CH_2$=C(R)C(O)—A—, $CH_2$=C(R)—$CH_2$—O—, $CH_2$=C(R)—$CH_2$OC(O)—, $CH_2$=C(R)OC(O)—, $CH_2$=C(R)O—, and $CH_2$=C(R)$CH_2$OC(O)N($R^1$)— wherein:

R is hydrogen or a $C_1$–$C_4$ alkyl group;

A is —O— or —$NR^1$—, $R^1$ is hydrogen or a $C_1$–$C_4$ alkyl group

K is selected from the group consisting of —$(CH_2)_p$OC(O)—, —$(CH_2)_p$C(O)O—, —$(CH_2)_p$C(O)$NR^2$—, —$(CH_2)_p$$NR^2$C(O)O—, —$(CH_2)_p$OC(O)$NR^2$—, —$(CH_2)_p$$NR^2$C(O)$NR^2$—, (in which the groups $R^2$ are the same or different)—$(CH_2)_p$O—, —$(CH_2)_p$$SO_3$—, and, optionally in combination with $B^2$, a valence bond and p is from 1 to 12 and $R^2$ is hydrogen or a $C_1$–$C_4$ alkyl group.

17. An implant according to claim 16 in which $Y^2$ is $CH_2$=C(R)C(O)A in which R is H or $CH_3$ and A is —NH or —O—.

18. An implant according to claim 1 in which the polymer matrix has a dry thickness of at least 0.5 μm.

19. An implant according to claim 1 in which the nucleic acid is DNA or RNA.

20. An implant according to claim 1 in which the nucleic acid has a molecular weight higher than 1 kD.

21. An implant according to claim 6 in which the ratio of zwitterionic to cationic monomer is in the range 1:10 to 10:1.

22. An implant according to claim 1 which is a stent.

23. A method in which an implant according to claim 1 is placed in an environment comprising a liquid medium, whereby the pharmaceutical active is released into the liquid medium.

24. A method according to claim 23 in which the environment is in vivo in the body of an animal.

25. An implant according to claim 2 in which the polymer is formed from ethylenically unsaturated monomers including less than 20 mole % cross-linkable monomer.

26. An implant according to claim 2 in which the polymer is formed from ethylenically unsaturated monomers including a) a zwitterionic monomer of the formula I

YBX            I wherein B is a bond or a straight or branched alkylene, alkylene-oxa-alkylene or alkylene-oligooxa-alkylene group, any of which optionally include one or more fluorine substituents;

X is an organic group having a zwitterionic moiety; and

Y is an ethylenically unsaturated polymerisable group;

b) a cationic monomer of the formula II $Y^1B^1Q^1$            IV wherein $B^1$ is a bond or a straight or branched alkylene, alkylene-oxa-alkylene or alkylene-oligooxa-alkylene group, any of which optionally includes one or more fluorine substituents;

$Y^1$ is an ethylenically unsaturated polymerisable group; and

Q is an organic group having a cationic or cationisable moiety and c) a crosslinkable monomer having the general formula IV:

$Y^3B^3Q^3$            IV wherein $B^3$ is a bond or a straight or branched alkylene, alkylene-oxa-alkylene or alkylene-oligooxa-alkylene group, any of which optionally includes one or more fluorine substituents;

$Y^3$ is an ethylenically unsaturated polymerisable group; and $Q^3$ is an organic group having a reactive group capable of cross-linking the polymer.

27. An implant according to claim 26 in which $Q^3$ contains a crosslinkable moiety selected from the group consisting of cinnamyl, epoxy, —CHOHCH$_2$Hal in which Hal is a halogen atom, methylol, reactive silyl, ethylenically unsaturated, acetoacetoxy and chloroalkyl sulfone groups.

28. An implant according to claim 27, in which $Q^3$ is a group $SiR^4_3$ in which each $R^4$ is a $C_{1-4}$ alkoxy group or a halogen atom.

29. An implant according to claim 28 in which the monomers further include a compound of the formula IV'

$Y^3B^3Q^4$            IV' wherein $B^3$ is a bond or a straight or branched alkylene, alkylene-oxa-alkylene or alkylene-oligooxa-alkylene group, any of which optionally includes one or more fluorine substituents;

$Y^3$ is an ethylenically unsaturated polymerisable group and $Q^4$ is a hydroxyl group.

30. An implant according to claim 26 in which X is a group of formula VI

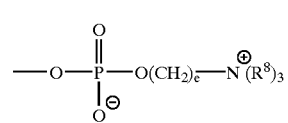

(VI)

where the groups $R^8$ are the same or different and each is hydrogen or $C_{1-4}$ alkyl, and e is from 1 to 6.

31. An implant according to claim 30 in which the groups Y, $Y^1$ and $Y^3$ all have the general formula $CH_2$=C(R)C(O)A— in which A is —O— or —$NR^1$ where $R^1$ is hydrogen or a $C_{1-4}$ alkyl group, and R is hydrogen or a $C_{1-4}$ alkyl group.

32. An implant according to claim 26 in which $Q^1$ is selected from the group consisting of $N^{32}R^5_3$, $P^-R^5_3$ and $S^-R^5_2$ in which the groups $R^5$ are the same or different and are each selected from the group consisting of hydrogen, $C_{1-4}$-alkyl and aryl, or two of the groups together with the heteroatom to which they are attached form a saturated or unsaturated heterocyclic ring containing from 5 to 7 atoms.

33. An implant according to claim 26 in which the monomers further include a termonomer of the formula III $$Y^2B^2Q^2 \qquad \text{III}$$

wherein $B^2$ is a bond or a straight or branched alkylene, alkylene-oxa-alkylene or alkylene-oligooxa-alkylene group, any of which may optionally include one or more fluorine substituents;
$Y^2$ is an ethylenically unsaturated polymerisable group; and
$Q^2$ is an organic group having a hydrophobic group selected from alkyl groups having at least six carbon atoms, fluorine substituted alkyl groups and alkyl groups having at least one siloxane substituent.

34. An implant according to claim 33 in which $Y^2$ is $CH_2C(R)C(O)A$ in which R is H or $CH_3$ and A is —NH or —O—.

35. An implant according to claim 26 in which the ratio of zwitterionic to cationic monomer is in the range 1:10 to 10:1.

36. An implant according to claim 2 which is a stent.

37. An implant according to claim 3 in which the polymer is formed from ethylenically unsaturated monomers including less than 20 mole % cross-linkable monomer.

38. An implant according to claim 3 in which the polymer is formed from ethylenically unsaturated monomers including
a) a zwitterionic monomer of the formula I $$YBX \qquad \text{I}$$

wherein B is a bond or a straight or branched alkylene, alkylene-oxa-alkylene or alkylene-oligooxa-alkylene group, any of which optionally include one or more fluorine substituents;
X is an organic group having a zwitterionic moiety; and
Y is an ethylenically unsaturated polymerisable group;
b) a cationic monomer of the formula II $$Y^1B^1Q^1 \qquad \text{II}$$

wherein $B^1$ is a bond or a straight or branched alkylene, alkylene-oxa-alkylene or alkylene-oligooxa-alkylene group, any of which optionally includes one or more fluorine substituents;
$Y^1$ is an ethylenically unsaturated polymerisable group; and
Q is an organic group having a cationic or cationisable moiety and
c) a crosslinkable monomer having the general formula IV:

$$Y^3B^3Q^3 \qquad \text{IV}$$

wherein $B^3$ is a bond or a straight or branched alkylene, alkylene-oxa-alkylene or alkylene-oligooxa-alkylene group, any of which optionally includes one or more fluorine substituents;
$Y^3$ is an ethylenically unsaturated polymerisable group; and
$Q^3$ is an organic group having a reactive group capable of cross-linking the polymer.

39. An implant according to claim 38 in which $Q^3$ contains a crosslinkable moiety selected from the group consisting of cinnamyl, epoxy, —CHOHCH$_2$Hal in which Hal is a halogen atom, methylol, reactive silyl, ethylenically unsaturated, acetoacetoxy and chloroalkyl sulfone groups.

40. An implant according to claim 39 in which $Q^3$ is a group $SiR^4_3$ in which each $R^4$ is a $C_{1-4}$ alkoxy group or a halogen atom.

41. An implant according to claim 40 in which the monomers further include a compound of the formula IV'

$$Y^3B^3Q^4 \qquad \text{IV'}$$

wherein $B^3$ is a bond or a straight or branched alkylene, alkylene-oxa-alkylene or alkylene-oligooxa-alkylene group, any of which optionally includes one or more fluorine substituents;
$Y^3$ is an ethylenically unsaturated polymerisable group and $Q^4$ is a hydroxyl group.

42. An implant according to claim 28 in which X is a group of formula VI

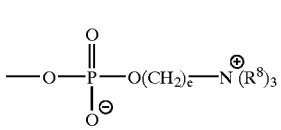

where the groups $R^8$ are the same or different and each is hydrogen or $C_{1-4}$ alkyl, and e is from 1 to 6.

43. An implant according to claim 42 in which the groups Y, $Y^1$ and $Y^3$ all have the general formula $CH_2$=C(R)C(O) A— in which A is —O— or —$NR^1$ where $R^1$ is hydrogen or a $C_{1-4}$ alkyl group, and R is hydrogen or a $C_{1-4}$ alkyl group.

44. An implant according to claim 38 in which $Q^1$ is selected from the group consisting of $N^+R^5_3$, $P^+R^5_3$ and $S^+R^5_2$
in which the groups $R^5$ are the same or different and are each selected from the group consisting of hydrogen, $C_{1-4}$-alkyl and aryl, or two of the groups together with the heteroatom to which they are attached form a saturated or unsaturated heterocyclic ring containing from 5 to 7 atoms.

45. An implant according to claim 38 in which the monomers further include a termonomer of the formula III $$Y^2B^2Q^2 \qquad \text{III}$$

wherein $B^2$ is a bond or a straight or branched alkylene, alkylene-oxa-alkylene or alkylene-oligooxa-alkylene group, any of which may optionally include one or more fluorine substituents;
$Y^2$ is an ethylenically unsaturated polymerisable group; and
$Q^2$ is an organic group having a hydrophobic group selected from alkyl groups having at least six carbon atoms, fluorine substituted alkyl groups and alkyl groups having at least one siloxane substituent.

46. An implant according to claim 45 in which $Y^2$ is $CH_2C(R)C(O)A$ in which R is H or $CH_3$ and A is —NH or —O—.

47. An implant according to claim 38 in which the ratio of zwitterionic to cationic monomer is in the range 1:10 to 10:1.

48. An implant according to claim 3 which is a stent.

49. An implant according to claim 20, in which the nucleic acid has a molecular weight higher than 1.2 kD.

50. An implant according to claim 19 in which the nucleic acid is linear or circular, single or double stranded.

* * * * *